United States Patent [19]

Snyder et al.

[11] Patent Number: 4,937,797
[45] Date of Patent: Jun. 26, 1990

[54] METHOD AND APPARATUS FOR CONTROLLING SCAN LINE DIRECTION IN A LINEAR ARRAY ULTRASONIC DOPPLER SCANNING SYSTEM

[75] Inventors: Richard A. Snyder, Chester, N.H.; Martin J. Moynihan, Stoneham, Mass.

[73] Assignee: Hewlett-Packard Company, Palo Alto, Calif.

[21] Appl. No.: 270,572

[22] Filed: Nov. 14, 1988

[51] Int. Cl.$^5$ .................................. H04B 1/02
[52] U.S. Cl. ........................... 367/138; 367/7; 128/661.01; 128/661.08
[58] Field of Search ................ 367/95, 96, 103, 105, 367/138, 12, 7; 128/660.01, 661.01, 661.08, 661.09, 661.1; 364/413.07

[56] References Cited

U.S. PATENT DOCUMENTS

4,630,612 12/1986 Uchida et al. ............... 128/661.09
4,817,619 4/1989 Sugiyama et al. ........... 128/661.09

Primary Examiner—Thomas H. Tarcza
Assistant Examiner—Daniel T. Pihulic
Attorney, Agent, or Firm—Frank R. Perillo

[57] ABSTRACT

This invention relates to a method and apparatus for automatically controlling scan line direction in a linear array ultrasonic Doppler scanning system. More particularly, this system determines an ideal scan line angle and point of origin for a given sample volume having fluid flow in a given direction. The system then determines left and right limiting angles for the given sample volume taking into account the geometry of the viewing area relative to the sample volume and the maximum steering angle of the transducers of the transducer array being utilized. Where, because of pulse repetition rate considerations, a maximum depth from the sampling aperture of the linear array to the sample volume exists, this maximum depth is also taken into account in determining the limiting angles. The system then uses the ideal angle as a scan angle is such ideal angle is between the limiting angles and utilizes a selected one of the limiting angles determined in accordance with predetermined criteria, if the ideal angle is outside the limiting angles. Once the scan angle has been determined, this angle may be utilized to identify the aperture to be utilized for the given scan.

21 Claims, 4 Drawing Sheets

FIG 4

METHOD AND APPARATUS FOR CONTROLLING SCAN LINE DIRECTION IN A LINEAR ARRAY ULTRASONIC DOPPLER SCANNING SYSTEM

FIELD OF THE INVENTION

This invention relates to linear array ultrasonic Doppler scanning systems and more particularly to a method and apparatus for automatically controlling the scan line direction and point of origin in such a system.

BACKGROUND OF THE INVENTION

Linear array ultrasonic scanning systems are utilized in a variety of applications including medical imaging. A particular application of such systems is to utilize the Doppler effect to determine the direction and, more importantly, the rate of flow of a fluid such as blood at a gate or sample volume point. Such a system may for example operate by applying bursts of pulses at a selected repetition rate from a selected subset or aperture of the ultrasonic transducers of the linear array to the sample volume of the subject being examined. By positioning the sample volume at a selected point or successive sequence of points along a vein or artery, it is thus possible to plot blood flow through such internal channel. Abnormalities in the rate of blood flow at a selected sample volume are indicative of various disease conditions such as a partial or total occlusion in such channel.

In order to take Doppler readings for a selected sample volume, it is necessary that the direction of the parallel scan lines from a selected aperture of the linear array transducers be at an angle to the direction of flow which is not 90° or 270° since it is not possible to obtain Doppler readings at these angles. For most applications, the ideal scan line angle is in a direction parallel to the direction of flow since this maximizes the Doppler difference. However, since extensive diagnostic tables exist for an assumed scan angle of 60° (or 150°) to the direction of blood flow, in some applications this may be the ideal scan direction angle rather than 0° or 180°.

While an ideal scan angle may exist, it is not always possible to utilize this angle for a variety of reasons. First, because of the position of the sample volume within the viewing area, it may not be possible to set the transducers at the ideal angle while still passing through the sample volume. A second potential problem is that the ideal angle may be greater than the maximum steering angle available for the transducers of the linear array. For example, the system may be designed to provide steering angles of only plus or minus 45° for the ultrasonic transducers. If the ideal scan angle for a given sample volume is greater than the available steering angle, an angle other than the ideal scan angle must be utilized for such sample volume.

Finally, the depth of the sample volume, which is defined as the distance from the center transducer of the transducer aperture for the scan to the sample volume, is one factor in determining the time required for a pulse to reach the sample volume and for an echo of such pulse to return to the transducer. This round trip time for a sampling pulse determines the maximum pulse repetition rate available for the scan. The pulse repetition rate in turn determines the maximum blood flow rate which may be detected by the system. Thus, where because of diseased arteries or other blood flow channels, a high blood flow rate may be anticipated, and thus a high pulse repetition rate from the Doppler linear array may be required, depth may become a limiting factor on the angle which can be utilized for a given scan, particularly if the blood channel of interest is not near the skin surface.

Thus, when doing Doppler measurements with an ultrasonic linear array system, it is desirable that it be possible to select a scan line for the scan of a given sample volume which is as close as possible to the ideal angle from the direction of blood flow at the sample volume, provided that the depth from the aperture being used on the transducer array to the sample volume at the selected angle does not exceed the depth which would permit a desired pulse repetition rate for the Doppler scan.

Heretofore, the selection of the scan direction for Doppler scanning has been done manually. In particular, the angle for the scanning beam has been fixed at, for example, 60°, and the system operator has been able to manually move the transducer aperture until an aperture is found which causes the beam to pass through the selected sample volume. The system operator thus could not control the angle to achieve a desired angle and, in the remote case where the fixed direction of the beam happened to be perpendicular to the direction of blood flow, the system could not be utilized. In most instances the angle utilized was not the ideal angle, or even near the ideal angle, for the particular sample volume. Further, if the depth at the fixed angle turned out to be greater than the depth required in order to achieve a desired pulse repetition rate, there was no easy way to compensate for this and a lower pulse repetition rate would have to be utilized. The only other option would be to reposition the transducer array on the patient and start over.

Thus, even though such systems provide only limited control over Doppler beam direction and a beam direction which could be far from optimum, adjusting the beam for each scan is still a relatively time consuming process. The time required to make the manual adjustments could become a problem where, as is frequently the case, a large number of sequential readings are taken along a blood channel.

A need therefore exists for a relatively simple and rapid method and apparatus for permitting the optimum available scan angle to be achieved for each Doppler measurement, with the optimum available angle being determined taking into account all factors including the maximum steering angle of the transducers, the position of the sample volume within the field of view of the transducers and the maximum depth available to achieve a desired pulse repetition rate.

SUMMARY OF THE INVENTION

In accordance with the above, this invention provides a method and apparatus for controlling the Doppler scan line direction and point of origin in a linear array ultrasonic scanning system. The sample volume at which a Doppler determination is to be made is identified and the flow direction at the sample volume is designated. Utilizing the designated flow direction, a determination is made as to the ideal scan line (i.e., either a line parallel to the direction of blood flow or a line 60° (or 150°) to such direction depending on the mode of operation of the system). Left and right hand limit angles are then defined for the scanning of the sample volume by the array. If the ideal scan line direction is between the left and right hand limit angles, the ideal scan line is selected as the scan line direction. If the ideal scan line is not between the left and right hand limit angles, a selected one of the limit angles is designated as the scan line direction. More particularly, four quadrants are defined by intersecting lines passing through the sample volume and which bisect the angle between the left and right limit angles and are perpendicular to such bisector line. The quadrants are sequentially numbered in a clockwise direction starting with the upper right hand quadrant, the right hand limit angle being designated as the scan line direction if the ideal scan line is in the first or third quadrant and the left hand limit angle being designated if the ideal scan line is in the second or fourth quadrant. Once a scan line direction to the sample volume has been determined, this scan line direction may be utilized to determine the scan aperture for the linear transducer array.

The limit angles for a given sample volume are determined by determining for each limit angle, the angle from the sample volume to the corresponding corner of the array and the maximum steering angle of the array in the respective direction. The smaller of the corner angle or steering angle so determined is then selected as the corresponding limit angle. A maximum depth may be defined and the angle from the array to the sample volume which results in such maximum depth is also determined. If for a given limit angle, the angle which results in maximum depth is less than either the corner angle or the steering angle, then such minimum depth angle is selected as the limiting angle.

The foregoing and other objects, features and advantages of the invention will be apparent from the following more particular description of a preferred embodiment of the invention as illustrated in the accompanying drawings.

DETAILED DESCRIPTION

Figure 1:
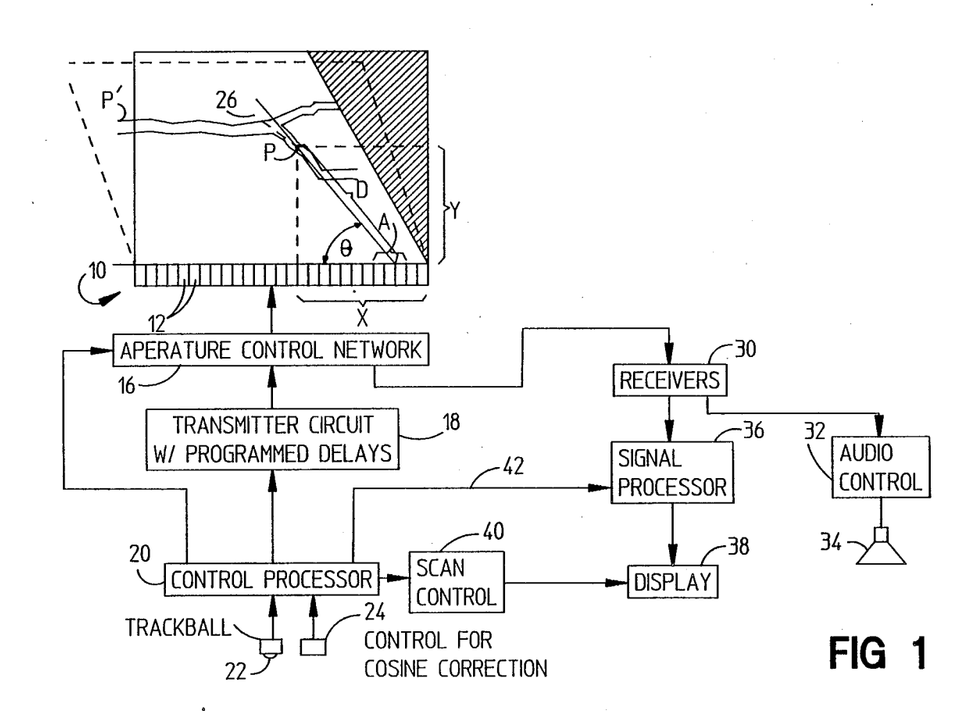
FIG. 1 is a semi-schematic block diagram of a system in which the teachings of this invention may be utilized, including a schematic representation of a portion of the patient's body on which a scan is being performed.

Referring to FIG. 1, an ultrasonic scanning system in which the teachings of this invention may be utilized is shown. This system includes an array 10 of transducer elements 12. Each transducer element 12 is adapted to both transmit ultrasonic pulse signals and to receive the echoes of such pulse signals. The number of transducer elements 12 forming a given array will vary with application but may for example be several hundred closely spaced piezoelectric elements.

As is illustrated in FIG. 1, the array 10 is used both to form a two dimension image of a viewing area V being scanned, which image may for example appear on a CRT display 38, and to perform a Doppler scan to detect blood flow direction and rate at a sample volume or gate P. The field of view V is determined by both the array steering angle and the depth or extent of the image, and serves as a reference for Doppler determinations.

A selected group or subset of the transducer elements 12 are selected as the aperture for transmission of ultrasonic pulses for a given ultrasonic scan. The number of transducer elements in the aperture A may again vary with application, with eight transducers, sixteen transducers, and thirty-two transducers being typical sizes for the aperture.

The size, and in particular the location of the aperture may be controlled by an aperture control switching network 16. Pulses to energize selected transducers 12 are applied from transmitter circuit 18 through aperture control network 16 to energize the transducers of a selected aperture. Transmitter circuit 18 includes programmed delays which, in a known fashion, are operative to control the scan angle of the ultrasonic transducers.

Both the aperture control network 16 and the transmitter circuit, including the programmed delays, are controlled from a control processor 20. Processor 20 may for example be a microprocessor or miniprocessor which is programmable to perform desired functions. Among the controls to processor 20 are a track ball control 22 which may be utilized to move a cursor to a selected sample volume point, for example the point P in FIG. 1, in the viewing area V and a suitable control 24 for a cosine correction cursor 26. This control may, for example, be a switch or button which causes the cursor to rotate when operated until the cursor is aligned in the direction of blood flow at the sample volume point P. The switch or button may then be released causing the cursor to remain in this orientation. The cosine correction or flow direction cursor may also be aligned in other ways known in the art.

Each burst of ultrasonic pulses from the transducers 12 of aperture A cause echoes or reflections from points along the beam path, including the sample volume point P, which echoes are received by the transducers. Since the depth D to the sample volume P is known, the echoes from the sample volume may be detected in standard fashion in the system. The echo signals from aperture A are passed through control network 16 to receivers 30. Some processing or filtering of the signals may be performed in known fashion at the receivers.

The received echo signals may be utilized to obtain a Doppler difference signal indicative of the velocity of blood flow at the sample volume which difference may be communicated in at least two ways. One standard way of recognizing such difference is to convert the Doppler difference into an audio signal in audio control 32, the frequency and thus the tone of such audio signal varying as a function of the Doppler difference. The output from the audio control is applied to control a speaker 34 through which the operator may listen to the tone generated. An increase in the pitch of this tone may, for example, indicate an increase in the rate of blood flow and thus a potential occlusion or other problem.

The second standard way to utilize the Doppler difference received and detected at receivers 30 is to pass such signal through a signal processing circuit 36 to control a spectrograph display on display 38. The scan of such display may be controlled from a standard scan control circuit 40 with timing signals from control processor 20. The signals from control processor 20 permit the display to be synchronized with the scan by transducers 12. The spectrograph display indicates the degree of positive and/or negative Doppler shift with time. Since the direction of Doppler shift can depend not only on the direction in which blood is flowing but also on the direction of scan, a line 42 is provided from control processor 20 to signal processor 36 to assure that the direction of the spectrograph display does not shift merely because of a change in scan direction.

The system described to this point is for the most part fairly standard. As previously indicated, with existing systems of this type, the scan angle $\theta$ for the scan direction is typically fixed and the beam is positioned to pass through the sample volume P by moving the aperture A along the linear array 10 until a position is found where the beam will pass through the sample volume.

As was discussed above, this procedure has a number of limitations. For one thing, sample volumes located in shaded area 46 of the field of view cannot be sampled since there is no way to position the beam to this region. Second, the beam angle $\theta$ is normally not optimum for any direction of blood flow and, in the rare instance where the direction of this beam is perpendicular to the direction of blood flow, the system will not operate. Quite frequently, the system operates by merely assuming a particular angle between the scan beam and the direction of blood flow, for example, 60°, and the generated audio output or display is based on this assumption. For at least some sample volumes, this assumption may be sufficiently erroneous as to lead to false readings or conclusions and in most instances, the assumption is sufficiently off to result in erroneous readings. Such errors may compromise the accuracy of medical determinations made utilizing such readings.

Further, with the angle $\theta$ fixed, there is only a single aperture along array 10 which may be utilized for a given sample volume P. If use of this aperture results in a depth D which is too long to achieve a desired pulse repetition rate, the system does not provide an easy way to overcome this problem.

Finally, since the position of the aperture is manually controlled (utilizing a control not shown in FIG. 1), a finite time is required to position the aperture for each selected sample volume, which time will vary with the skill of the operator. This reduces the rate at which readings may be taken and increases the work which must be done by the operator for each reading.

Figure 2:
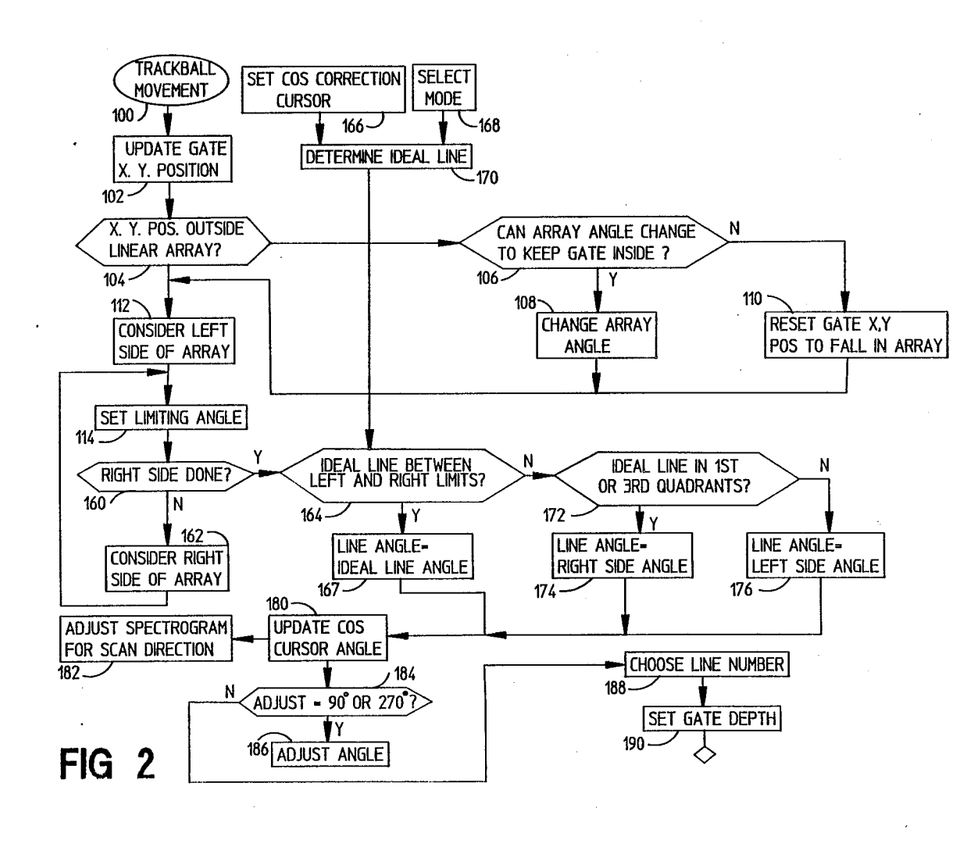
FIG. 2 is a flow diagram of the method of controlling the Doppler scan line direction of this invention.

The problems indicated above are solved by the Doppler scan line control method and apparatus of this invention. FIG. 2 is a general flow diagram of this method. In particular, referring to FIG. 2, during step 100 track ball control 22 is operated to position a sample volume cursor in the viewing area displayed on the screen of display 38 to a desired sample volume point P. The system, during step 102, records the X and Y positions of the point P in the viewing area. It should be noted that in FIG. 2 the term "gate" is utilized which term, for purposes of this invention, will be considered to be synonymous with the term "sample volume".

During the next step in the operation, step 104, a determination is made as to whether the X, Y position selected for the sample volume P is within the field of view of linear array 10. If it is determined that the X, Y position of the point P is outside the field of view, for example, the point P' shown in FIG. 1, the operation branches to step 106 during which a determination is made as to whether the steering angle of array 10 can be changed to bring the point P' within the field of view. This may be accomplished by, for example, changing the array angle to that shown by dotted lines in FIG. 1. The array angle may be changed in known fashion by modifying the programmed delays within circuit 18.

If during step 106 it is determined that the array steering angle can be changed to bring the point P' within the field of view, the array steering angle is changed under control of control processor 20 during step 108. However, if the change in array angle necessary to bring the point P' within the field of view is greater than the permitted steering angle for array 10, for example, greater than 45°, then a determination will be made during step 106 that the point P' cannot be brought within the field of view and the operation will proceed to step 110 during which one of two things will happen. The first thing that can happen during step 110 is for the system to automatically move the point P' to the closest point thereto which is within a possible field of view. The second option is to advise the operator under these conditions that the point selected is outside the available field of view and to permit the operator to either select another point or to reposition the array 10 relative to the patient so that the point P' is brought within the field of view.

Figure 3:
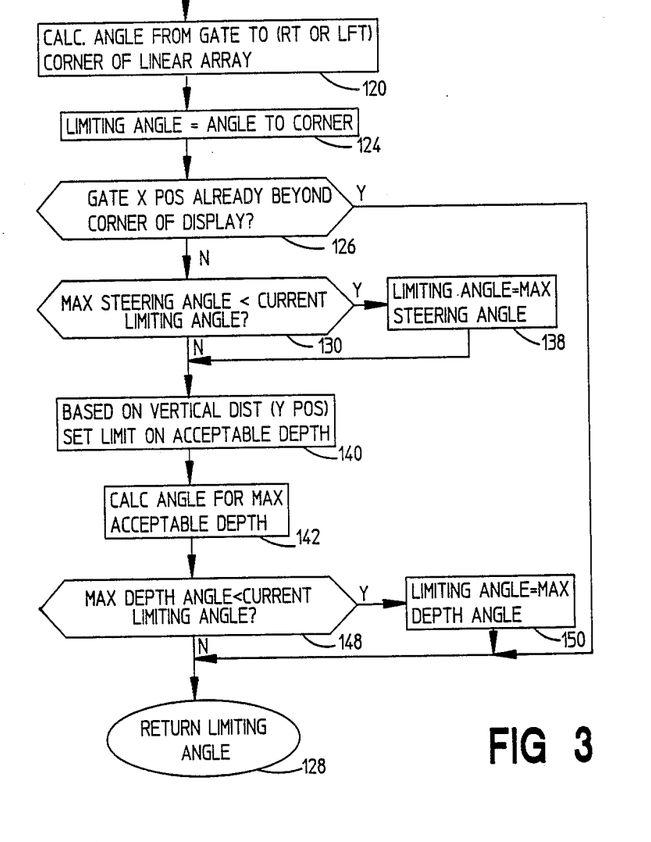
FIG. 3 is a flow diagram of the "set limiting angle" step of FIG. 2.
Figure 4:
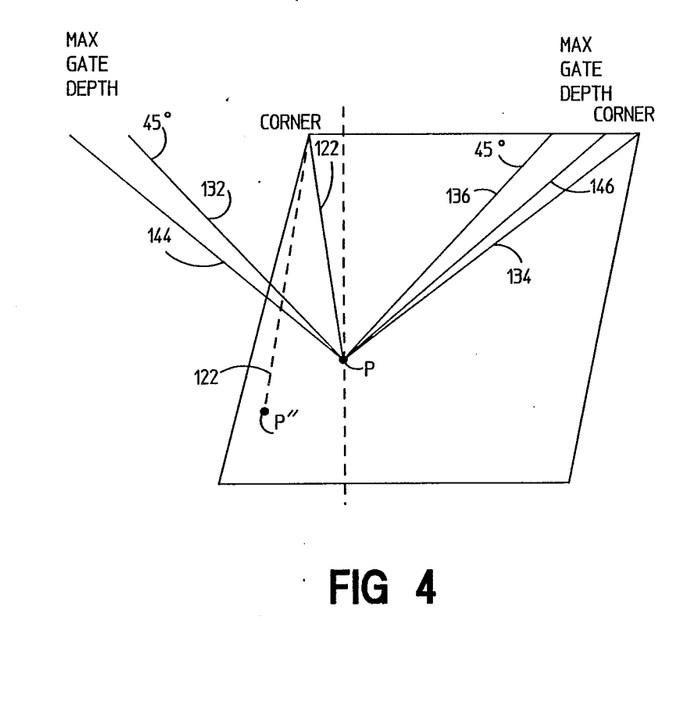
FIGS. 4 and 5 are diagrams illustrating the operation of the method and apparatus of this invention.

Once a point P within the field of view of the array 10 has been selected, the operation proceeds to step 112 during which the left side of the array is looked at and to step 114 during which the limit angle for the left side of the array is set. FIG. 3 is a flow diagram illustrating the sequence of operations which is performed during the "set limiting angle" step 114 of FIG. 2. FIG. 4 is a diagram illustrating the operations performed in FIG. 3.

During step 120, the first step in the "set limiting angle" operation, the angle from the sample volume point P to the left corner of the array is calculated. This is the line 122 shown in FIG. 4. During the next step in the operation, step 124, the left limiting angle is initially set to be this left corner angle.

During step 126, a determination is made as to whether the sample volume point P is beyond the corner of the display. For example, a "yes" output would be obtained during step 126 if the point being looked at was the point P" rather than the point P. Under this circumstance, the left limiting angle would be the angle of the corner line 122" shown in FIG. 4 and the operation would proceed to step 128 during which this angle would be stored as a left limiting angle and the operation would return to FIG. 2.

If during step 126 a determination is made that the point P is not beyond the corner of the display, the operation proceeds to step 130 during which a determination is made as to whether the maximum steering angle is less than the current limiting angle. In FIG. 4, it is assumed that the maximum steering angle is 45°. Thus, while for the left limiting angle, the corner angle is less than the maximum steering angle as represented by the line 132; for the right side, the corner angle as represented by the line 134 is greater than the limiting angle represented by the line 136. Thus, while for the left side a "no" output would be obtained during step 130, when the limiting angle is being set for the right side, a "yes" output would be obtained during this step. If a "yes" output is obtained during step 130, the operation proceeds to step 138 to set the limiting angle equal to the maximum steering angle. Thus, at this stage in the operation, the limiting angle has been set to the lesser of either the corner angle or the maximum steering angle.

From step 130 if a "no" output is obtained, or from step 138, the operation proceeds to step 140 during which, if necessary, a limit is set on acceptable depth D in order to obtain a desired pulse repetition rate. During step 142, the next step in the operation, the angle from array 10 to point P for the maximum acceptable depth D is calculated. For the left side in FIG. 4, this is represented by the line 144 and for the right side it is represented by the line 146. The operation then proceeds to step 148 during which a determination is made as to whether the maximum depth angle is less than the current limiting angle. If the maximum depth angle is determined during step 148 to be less than the current limiting angle (which is the lesser of the corner angle or the maximum steering angle) then the operation proceeds to step 150 during which the limiting angle is set to be equal to the maximum depth angle. Thus, when step 148 (and step 150 if necessary) have been completed, the limiting angle has been set equal to the angle which is the lesser of the corner angle, the maximum steering angle, or the maximum depth angle. This is the desired limiting angle. From FIG. 4, it is seen that, for the left side, the limiting angle is the corner angle as represented by line 122 while, for the right side, the limiting angle is the maximum swing angle as represented by the line 136. From step 148 or 150, the operation proceeds to step 128 to store the determined limiting angle and to return to FIG. 2.

When step 128 of step 114 (FIG. 2) has been completed, the operation proceeds to step 160 to determine if the right side limiting angle has been set. If the right side limiting angle has not been determined, the operation proceeds to step 162 to consider the right side of the array and then returns to step 114 to determine the limiting angle for the right side of the array. As before, the sequence of the operations set forth in FIG. 3 is performed to set the right side limiting angle. This procedure is also illustrated in FIG. 4 and was discussed previously.

When, during step 160, it is determined that both limiting angles have been set, the operation proceeds to step 164. Prior to commencing the operation, or at least at some time prior to performing step 164, cosine correction vector 26 is also set to indicate the direction of blood flow at the point P. This is illustrated by step 166. At the same time, a mode switch is operated to indicate whether the system is to operate in a "line lock" mode in which the ideal line is at an angle of 60° (or 150°) to the direction of the cosine correction cursor, or whether the system is to operate in normal mode (i.e., not line lock mode) in which case the ideal line is parallel to (i.e., 0° or 180°) to the direction of blood flow (i.e., the direction of the cosine correction cursor 26). The mode selection is made during step 168. From the selected mode and the cosine correction cursor direction, the ideal line for the given sample volume and the given mode is determined during step 170.

This ideal line direction is utilized during step 164 to determine if the ideal line is between the left and right limit angles determined during step 114. In other words, referring to FIG. 5, a determination is made as to whether the ideal line is in the shaded area shown in this figure. If the ideal line is in this shaded area between the left and right limit angles, then it is possible for the scan line to be at the same angle as the ideal line. Thus, if a "yes" output is obtained during step 164, the operation proceeds to step 167 during which the line angle is set equal to the ideal line angle.

Figure 5:
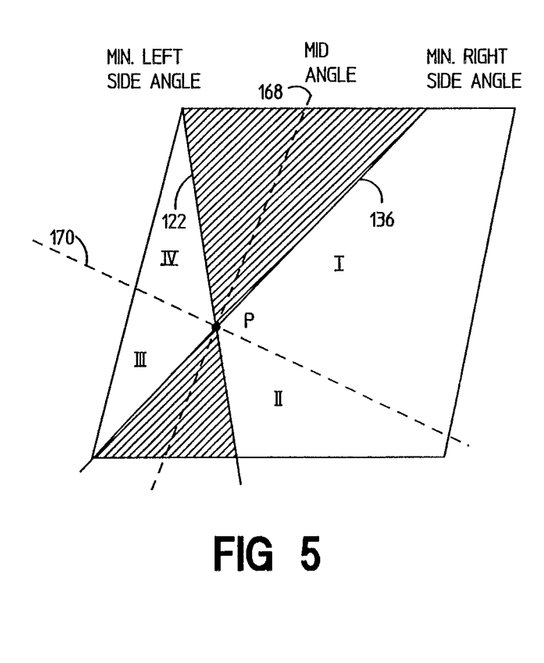

If the ideal line angle does not fall between the left and right limiting angles, then it is not possible to have the line angle equal to the ideal line angle and the best compromise which can be achieved is to utilize the closest limiting angle to the ideal line angle as the actual line angle. In accordance with the teachings of this invention, this is accomplished by dividing the area of view into four quadrants, this being accomplished by a line 168 which bisects the angle between the left and right limiting angle lines and a line 170 perpendicular to the line 168, which lines intersect at the sample volume point P. The quadrants are sequentially numbered in a clockwise direction as shown starting with the upper right hand quadrant.

Thus, if a "no" output is obtained during step 164, the operation proceeds to step 172 to determine if the ideal line is in the first or third of the quadrants shown in FIG. 5. If the ideal line is in the first or third quadrant, the line angle selected is the right side limiting angle which is the line 136 from FIG. 4. This selection is made during step 174. If during step 172 it is determined that the ideal line is not in the first or third quadrants, this means that the line must be in the second or fourth quadrant. Under these conditions, the operation proceeds to step 176 to select the left side limiting angle as the line angle. In FIG. 5, this is the line 122 which is the same as the line 122 shown in FIG. 4.

From step 166, 174 or 176, the operation proceeds to step 180 to update the cosine cursor angle. The purpose of this step is to determine the angle between the scan line selected during step 166, 174 or 176 and the cosine cursor 26. This angle can be easily determined from the known angles between each of these vectors and the face of array 10.

From step 180, the operation proceeds in two directions to perform two separate functions. First, the operation proceeds to step 182 to adjust the spectrogram display on display 38 if necessary, for scan direction. As previously indicated, the spectroqraph displays either positive or negative Doppler shift as a function of time. Thus, if the direction of scan is between 270° and 90° of the direction of blood flow (i.e., has a vector in the direction of blood flow), the Doppler shift will be negative, while if the scan line is between 90° and 270° of the direction of blood flow (i.e., has a vector in the direction opposite to the direction of blood flow) the Doppler shift will be positive. During step 182 a signal is applied to line 42 (FIG. 1) so as to prevent a shift in the direction of the spectrograph because of a change in scan direction, it being desired that a change in the spectrograph direction occur only in the event there is a change in the direction of blood flow.

In addition, from step 180, the operation also proceeds to step 184 to determine if the angle determined during step 180, (i.e., the angle between the scan line and the direction of blood flow) is equal to 90° or 270°. Since Doppler readings cannot be taken when the scan line is perpendicular to the direction of blood flow, if a "yes" determination is made during step 184, the operation proceeds to step 186 to make a slight adjustment in the scan angle. This adjustment would normally be to increase or decrease the angle by 1°. Flexibility may be required as to whether an increase or decrease occurs during step 186 since, where the line angle is a limiting angle, adjustment in only one of the directions will be possible. While the line being used for the scan where step 186 has been performed is far from ideal, it will provide a usable Doppler output.

From step 184 if a "no" output is obtained, or from step 186 if this step is performed, the operation proceeds to step 188 during which a determination is made as to the center point of the aperture A. This determination is easily made from the X and Y coordinates of the point P and from the selected line angle, all of which are known at this point in the operation.

Finally, from step 188, the operation proceeds to step 190 during which the depth D is determined for the selected sample volume P and scan line at angle θ. Again, this value can be easily determined from the X and Y coordinates of the point P and either the X and Y coordinates at the center of the aperture A or the angle θ. As previously indicated, the depth D is required both to determine the maximum pulse repetition rate available for the particular scan and to properly trigger the receiver to recognize echo pulses from the point P.

Once step 190 has been completed, the system is ready to take Doppler readings at the point P in standard fashion. When readings at a given point P have been completed, the sample volume cursor P may be moved to a new point by the user operating track ball 22, the user may indicate the direction of blood flow at this point by operating control 24, and the system will then rapidly repeat the sequence of operations described above in conjunction with FIGS. 2–5 in order to establish the optimum scan angle for this next sample volume point. A sequence of Doppler readings may therefore be quickly and easily taken along a body channel with the operator performing minimum steps between each reading.

A system has thus been provided which quickly determines the optimum Doppler scan angle for each successive sample volume in an ultrasonic linear array scanning system. The optimum angle takes into account the direction of blood flow at the sample volume point and seeks to the extent possible to have an ideal scan angle for such direction of blood flow for the mode of operation in which the system is being operated or as close to the ideal angle as is possible taking into account the geometric limitations of the scan area, the steering angle limitations of the transducers being utilized and, where necessary, the depth limitations of the system in order to achieve a desired pulse repetition rate.

While the invention has been described above for a preferred embodiment, the foregoing and other changes in form and detail may be made therein by one skilled in the art without departing from the spirit and scope of the invention.

What is claimed is:

1. A Doppler scan line direction controller for a scanning system having a linear array of ultrasonic transducers adapted to scan a selected sample volume at which a fluid is flowing in a predetermined direction, the controller comprising:
    means for identifying the sample volume at which a Doppler determination is to be made;
    means for designating the flow direction at said sample volume;
    means responsive to said designated flow direction for designating an ideal scan line;
    means for defining left and right limit angles for scanning of the sample volume by the array of transducers;
    means operative if the ideal scan line is at an angle between said left and right limit angles for selecting the ideal scan line as the scan line direction; and
    means operative if the ideal scan line is at an angle which is not between said left and right limit angles for designating a selected one of said limit angles as the scan line direction.

2. A controller as claimed in claim 1 wherein an aperture defined by a selected adjacent subset of the transducers of said linear array perform each Doppler scan; and
    including means operative in response to the selected scan line direction through the sample volume for defining the aperture for a given scan.

3. A controller as claimed in claim 1 wherein quadrants are defined by lines intersecting at the sample volume, one of which lines is the bisector for the angle between the left and right limit angles and the other of which is perpendicular to the bisector line; and
    wherein with the quadrants being numbered sequentially in the clockwise direction starting with the upper right hand quadrant, said means for designating a selected one of the limit if angles includes means for designating the right limit angle of the ideal scan line is in the first or third quadrant, and means for designating the left limit angle if the ideal scan line is in the second or fourth quadrant.

4. A controller as claimed in claim 1 wherein the ideal scan line is designated to be the flow direction through the sample volume.

5. A controller as claimed in claim 1 wherein the ideal scan line is designated to be at a 60° or 150° angle to the flow direction through the sample volume.

6. A controller as claimed in claim 1 wherein the means for defining the limit angles includes means operative for each limit angle for determining the angle from the sample volume to the corresponding corner of the array, means for defining the maximum steering angle of the array in the respective direction, and means for selecting the smaller of said corner angle or said steering angle as the corresponding limit angle.

7. A controller as claimed in claim 6 wherein an aperture defined by a selected adjacent subset of the transducers of said linear array perform each Doppler scan;
    wherein a maximum depth is defined from said aperture to the sample volume;
    wherein said means for defining the limit angles includes means operative for each limit angle for determining the angle from the array to the sample volume for which the depth equals said maximum depth, and
    wherein said means for selecting selects the determined angle for maximum depth if that angle is smaller than the corresponding corner angle and steering angle.

8. A controller as claimed in claim 6 including a means operative for each limit angle determination for detecting if the sample volume is beyond the corresponding corner, and means responsive to a detection by said detection means for selecting the corner angle as the limit angle for the corresponding side.

9. A controller as claimed in claim 1 wherein said linear array has a selected steering angle which defines the area which may be viewed by the array; and
    including means for determining if the sample volume is within the viewing area, and means responsive to a determination that the sample volume is outside the viewing area for adjusting the steering angle.

10. A controller as claimed in claim 1 including means for determining if the angle between the selected scan line direction and the designated flow direction is 90° or 270°, and means responsive to a determination that the angle between the scan line and flow direction is 90° or 270° for adjusting the scan line direction.

11. A method of controlling Doppler scan line direction in a linear array ultrasonic scanning system comprising the steps of:
    identifying a sample volume at which a Doppler determination is to be made;

designated a flow direction at the sample volume;

utilizing the flow direction to determine an ideal scan line;

defining left and right limit angles for the scanning of the sample volume by the array;

selecting the ideal scan line as the scan line direction if the ideal scan line is at an angle between the left and right limit angles; and designating a selected one of the limit angles as the scan line direction if the ideal scan line is at an angle which is not between the left and right limit angles.

12. A method as claimed in claim 11 wherein each Doppler scan is performed by an aperture defined by a selected adjacent subset of transducers forming said linear array; and including the step of defining the aperture for a given scan in response to the selected or designated scan line direction.

13. A method as claimed in claim 11 wherein quadrants are defined by lines intersecting at the sample volume, one of which which lines is the bisector for the angle between the left and right limit angles and the other of which is perpendicular to said bisector line; and wherein with the quadrants being numbered sequentially in the clockwise direction starting with the upper right hand quadrant, said designating scan line direction step includes the steps of designating the right hand limit angle as the scan line direction if the ideal scan line is in the first or third quadrant, and designating the left limit angle as the scan line direction if the ideal scan line is in the second or fourth quadrant.

14. A method as claimed in claim 11 wherein the ideal scan line is designated to be the flow direction through the sample volume.

15. A method as claimed in claim 11 wherein the ideal scan line is designated to be at a 60° or 150° angle to the flow direction through the sample volume.

16. A method as claimed in claim 11 wherein the defining limit angle step includes the steps operative for each limit angle of determining the angle from the sample volume to the corresponding corner of the array, defining the maximum steering angle of the array in the respective direction, and selecting the smaller of said corner angle or said steering angle as the corresponding limit angle.

17. A method as claimed in claim 16 wherein an aperture defined by a selected adjacent subset of the transducers of said linear array perform each Doppler scan;

wherein a maximum depth is defined from said aperture to the sample volume;

wherein said step of defining the limit angles includes the step performed for each limit angle of determining the angle from the array to the sample volume for which the depth equals said maximum depth, and wherein said selecting step selects the determined angle for maximum depth if that angle is smaller than the corresponding corner angle and steering angle.

18. A method as claimed in claim 16 wherein an aperture defined by a selected adjacent subset of the transducers of said linear array perform each Doppler scan; and including the step operative for each limit angle determination of detecting if the sample volume is beyond the corresponding corner, and selecting the corner angle as the limit angle for the corresponding side if it is determined that the sample volume is beyond the corresponding corner.

19. A method as claimed in claim 11 wherein said linear array has a selected steering angle which defines the viewing area which may be scanned by the array; and including the steps of determining if the sample volume is within the viewing area, and adjusting the steering angle if the sample volume is determined to be outside the viewing area.

20. A method as claimed in claim 11 including the steps of determining if the angle between the selected scan line direction and the designated flow direction is 90° or 270°, and adjusting the scan line direction if the angle between the scan line and flow direction is 90° or 270°.

21. A method as claimed in claim 11 wherein the results of the Doppler scan are displayed on a spectrogram; and including the step of controlling the spectrogram display to prevent a shift in the displayed spectrogram caused by a change in the direction of the scan line relative to the direction of flow.

* * * * *